United States Patent [19]

Elgavish

[11] Patent Number: 4,749,560

[45] Date of Patent: Jun. 7, 1988

[54] METAL ORGANO PHOSPHOROUS COMPOUNDS FOR NMR ANALYSIS

[75] Inventor: Gabriel A. Elgavish, Irondale, Ala.

[73] Assignee: Research Corporation, New York, N.Y.

[21] Appl. No.: 640,191

[22] Filed: Aug. 13, 1984

[51] Int. Cl.$^4$ .......................... A61K 49/00; A61B 6/00
[52] U.S. Cl. .......................................... 424/9; 128/653; 128/654; 534/10; 534/14; 534/15; 534/16; 556/13; 556/18; 556/19; 556/42; 556/45; 556/51; 556/57
[58] Field of Search .................... 556/18, 42, 45, 51, 556/57, 13, 19; 128/654, 653; 424/9; 534/10, 14, 15, 16

[56] References Cited

U.S. PATENT DOCUMENTS

| | | | |
|---|---|---|---|
| 3,477,953 | 11/1969 | Carlson | 556/19 |
| 3,534,125 | 10/1970 | Knollmueller | 558/161 |
| 3,983,227 | 9/1976 | Tofe et al. | 556/18 |
| 4,116,990 | 9/1978 | Budnick | 556/18 |
| 4,229,427 | 10/1980 | Whitehouse | 556/18 |
| 4,497,744 | 2/1985 | Fawzi | 556/18 |
| 4,647,447 | 3/1987 | Gries et al. | 424/9 |

FOREIGN PATENT DOCUMENTS 8633082  1/1983  Australia.

*Primary Examiner*—Robert J. Warden
*Assistant Examiner*—Stephen C. Wieder
*Attorney, Agent, or Firm*—Scully, Scott, Murphy & Presser

[57] ABSTRACT

The present invention relates to a class of compositions and a method for NMR imaging using an NMR signal affecting amount of a paramagnetic, diamagnetic or ferromagnetic metal ion chelated with an organo phosphorous compound.

Gadolinium bis(bis-dihydroxyphosphonylmethylphosphinate) is an example of such a composition.

12 Claims, No Drawings

METAL ORGANO PHOSPHOROUS COMPOUNDS FOR NMR ANALYSIS

DESCRIPTION

1. Technical Field

The loss of detail in NMR spectra can limit the use of NMR analysis. Contrast agents have been employed in order to improve NMR imaging for non-invasive clinical diagnoses of mammalian hosts. The present invention relates to a class of compositions and a method for NMR imaging using NMR signal affecting amounts of a paramagnetic, diamagnetic or ferromagnetic metal ion chelated with an organo phosphorous compound.

2. Prior Art

The use of rare earth metal ion chelates of beta-diketones as transparent NMR shift reagents are described by Belager et al. in U.S Pat. No. 3,818,061. The patentees describe the novel chelates as useful NMR shift reagents because they not only solublize the rare earth metal ion but additionally the beta-diketone ligand is substantially transparent or completely transparent to proton NMR analysis.

Compounds for affecting the relaxation time in NMR diagnostics is described by Gries et al. in European Patent Application No. 0 071 564. Phosphorous based chelated lanthanide metal ions are specifically disclosed by Gries et al.

Various bis-phosphinyl phosphinates are described as sequestrants by Knollmueller in U.S. Pat. No. 3,534,125. The patentee also describes that these phosphinates can be chelated with rare earth metal ions. Budnick, U.S. Pat. No. 4,116,990 and Carlson, U.S. Pat. No. 3,477,953 describe various phosphate chelating compounds as well.

NMR imaging has emerged in recent years as a superior technique for noninvasive clinical diagnosis of the heart, brain, kidney and other organs and tissues in mammalian hosts. In many instances, in order to obtain useful images, contrast enhancement is needed to delineate various aspects of the tissue especially normal as contrasted with abnormal tissue.

The prior art discloses that various techniques can be employed for affecting an NMR signal in a host, the most common of which is to introduce into the host a paramagnetic substance prior to NMR analysis or imaging. This is commonly achieved by employing polyvalent ions of a paramagnetic metal ion such as for example, iron, manganese, chromium, copper, nickel and metal ions of the lanthanide series. Gadolinium as a contrast agent for NMR has also been described by Caille' et al. (AJNR4: 1041–1042, September/October 1983) and that gadolinium is especially useful in this respect since it is the rare earth element that possess the highest paramagnetic moment, 10.8 Bohr magnetons. Although these ions of paramagnetic metal ions enhance NMR imaging, it has been reported that gadolinium is best used as a chelated ion to reduce its toxicity (Carr et al., The Lancet, Mar. 3, 1984 pp. 484–486). Additionally, Mendonca-Dias et al. (Seminars in Nuclear Medicine, Vol. XIII, No. 4 [October]1983 pp. 364–376) describe various paramagnetic contrast agents in nuclear magnetic resonance for medical imaging but caution against the use of copper, nickel and iron ions which have acute toxicities which are higher than manganese. The authors describe the long-term toxic effect of manganese (Managanism), as producing several neurologic and psychotic disorders, which in the late stages resembles Parkinson's disease. Lanthanide toxicity is also described by the authors and that a certain amount of precautions have to be employed when using metal ions from this group.

The authors disclose that toxicity is significantly reduced if the contrast enhancing metal ion ions are chelated or if they are selected so that only those that are flushed from the body rapidly are employed. If these ions are flushed too quickly from the body, their effectiveness in NMR analysis may be minimized or lost.

The contrast enhancing agents for medical NMR imaging are effective because the metal ion ions and their complexes may concentrate selectively in abnormal tissues, (Mendonca-Dias et al. vide supra) and the paramagnetic ions increase the relaxation rates of water protons at low concentration in the tissue. Chauncey et al., J. Nuel. Med., 1977; 18: 933–936 have also demonstrated the opposite in that radioactive $^{54}$Mn accumulated in normal myocardial that radioactive levels. tissue while infarcted myocardial tissue had reduced levels. As noted above, the use of some of these metal ion ions is not without its difficulties.

Many of the chelating agents used for paramagnetic, diamagnetic and ferromagnetic ions are not completely effective in keeping the ions complexed when administered to mammalian hosts since the complexes, during metabolism, can be broken down such as for example, in the use of phosphorous chelating agents which are in some instances hydrolyzed by phosphate-hydrolyzing enzymes abundant in living tissues.

It is therefore an object of the present invention to overcome these and other difficulties encountered in the prior art.

It is a further object of the present invention to provide a composition and a method for NMR analysis by use of a novel complex for affecting an NMR signal.

It is a further object of the present invention to provide a composition and a method for enhancing the detail in NMR spectra and contrast in NMR imaging.

It is a further object of the present invention to provide a novel composition and method for affecting an NMR signal employing a complex of a paramagnetic metal ion, diamagnetic metal ion or ferromagnetic metal ion and an organophosphorous chelating ligand which is not readily hydrolyzed by phosphate-hydrolyzing enzymes abundant in living tissues and which optionally enhances the NMR contrasting capability of the uncomplexed or nonchelated metal ion when such complex is administered to a host that is subsequently subjected to NMR analysis.

It is a further object of the present invention to provide a composition of matter and a method for NMR analysis comprising an NMR signal affecting amount of a complex of a paramagnetic metal ion, diamagnetic metal ion and a ferromagnetic metal ion and an organophosphorous metal ion chelating ligand which is relatively nontoxic in mammalian hosts, is not readily hydrolyzable by phosphate-hydrolyzing enzymes and will remain in a mammalian host relatively intact for a period of time sufficient to perform an NMR analysis on said host.

It is a further object of the present invention to provide the aforesaid complex and method wherein the complex concentrates selectively in abnormal tissues in a mammalian host to enhance the NMR analysis of such abnormal tissue.

It is a further object of the present invention to provide the aforesaid complex and method wherein the complex concentrates selectively in normal tissues which also contain abnormal tissue in a mammalian host to enhance the NMR analysis of the tissues.

These and other objects have been achieved according to the present invention which is more fully described in the specification that follows.

DETAILED DESCRIPTION OF THE PREFERRED EMBODIMENT OF THE INVENTION

The present invention relates to a method for enhancing NMR analysis comprising administering to a host an NMR signal affecting amount of a complex comprising a metal ion selected from a member of the group consisting of paramagnetic metal ions, diamagnetic metal ions and ferromagnetic metal ions and an organophosphorous metal ion chelating ligand comprising a phosphonylloweralkyl phosphinate. The preferred organophosphorous metal ion chelating ligand is not readily hydrolyzable by phophate-hydrolyzing enzymes. The host is then subjected to NMR analysis.

The NMR signal affecting amount of the complex is any amount of complex that will alter the spin-lattice, spin-spin or spin-echo relaxation times of an NMR signal. This alteration is effected in a manner in order to enhance the signals received from the specimen under analysis either by reducing the aforementioned relaxation times or by increasing them with respect to an area of the host or the host per se which has had the complex administered to it. In another embodiment, the NMR signal affecting amount of the complex is that amount which in addition to changing the relaxation times of the NMR signals in the host, will also change such relaxation times sufficiently so that sharper lines of definition or higher contrast is obtained between those parts of the host that have and have not been administered the complex.

The complex comprises a metal ion selected from a member of the group consisting of paramagnetic metal ions, diamagnetic metal ions and ferromagnetic metal ions.

The preferred metal ions employed in the complex of the present invention are paramagnetic metal ions since metal ions of this type generally have an enhanced relaxation effect on the surrounding water molecules in a mammalian host where the complex is taken up and generally, produce the enhanced contrast results in mammalian hosts which is a primary object of the present invention. Paramagnetic metal ions by definition are those metal ions that carry unpaired electrons.

Ferromagnetic metal ions may also be employed in this respect and include those metal ions whose internal magnetic moments spontaneously organize in a common direction.

Diamagnetic metal ions may also be employed which are those metal ions that do not carry unpaired electrons. These metal ions position themselves at right angles to magnetic lines of force, and include for example, the alkaline earth metal ions (Group IIA of the Periodic Table of the Elements) and the alkali metal ions (Group IA of the Periodic Table of the Elements). The preferred alkaline earth metal ions comprise magnesium, calcium, strontium and barium whereas the preferred alkali metal ions comprise lithium, sodium and potassium.

The preferred metal ions comprise the metal ions from the lanthanide group of the Periodic Table of the Elements and comprise those metal ions having atomic numbers 57-70 inclusive especially gadolinium and those metal ions having atomic numbers 21-29 inclusive and 42-44 inclusive especially copper, nickel, manganese, iron and chromium.

The especially preferred complexes of the present invention comprises water soluble anionic coordination-complexes, especially the water soluble anionic coordination-complexes of the lathanide metal ions.

The host to which the complex may be administered may be animate or inanimate. Either living or non-living tissue of an animate host may have the complex administered to it, although one of the principal objectives of the present invention is to provide a complex that is employed in a living host which is subject to NMR analysis and especially NMR imaging techniques.

The organophosphorous metal chelating ligand comprises a phosphonyl organophosphinate that complexes with a paramagnetic, diamagnetic or ferromagnetic metal ion to form complexes of the formula:

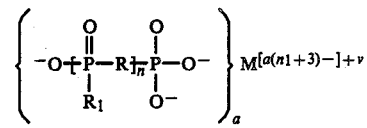

Where $n=2$ to about 100 and preferably from 2 to about 10

$n_1 =$ *the number of negative charges in*

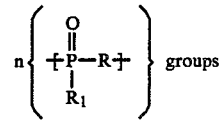

groups p1 M=a paramagentic, diamagnetic or a ferromagnetic metal ion

V=the valence of M $R_1=0^-$ or an organophosphinate comprising:

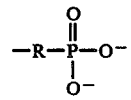

and preferably $0^-$ a=1, 2 or 3

R=alkyl, whether branched chain or straight chain, especially lower alkyl and preferably lower alkyl having from 1 to about 3 carbon atoms; cyclic hydrocarbon having from 3 to about 10 and especially 3 to about 6 carbon atoms, said cyclic hydrocarbon being saturated or unsaturated and including fused ring cyclic hydrocarbons; heterocyclic hydrocarbons having from 1 to about 2 heterocyclic nitrogen, phosphorous, sulfur or oxygen atoms in said heterocyclic ring, said heterocyclic hydrocarbon being saturated or unsaturated. a preferred complex is one of the formula:

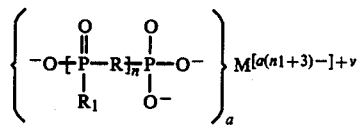

Where R is defined previously and especially where R comprises methyl, a, n, $n_1$ and v are defined previously and M is selected from a member of the group consisting of lanthanide metal ions, ions of the metals having atomic members 21 to 29 inclusive, 42 to 44 inclusive iron, cobalt, nickel, manganese, chromium and copper.

an especially preferred complex has the formula:

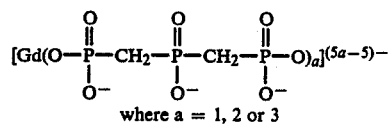

where a = 1, 2 or 3

The organophosphorous metal ion chelating ligand comprises a phosphonylloweralkyl phosphinate derived from phosphorous compounds comprising either bis-dihydroxy-phosphonylloweralkyl-phosphinic acid or tris-dihydroxy-phosphonylloweralkyl-phosphine oxide. In a preferred embodiment, the organophosphorous metal ion chelating ligand is not readily hydrolyzable by phosphate-hydrolyzing enzymes. The lower alkyl moiety includes straight or branch chain alkyl radicals where the straight chain alkyl radicals are preferred, in which the lower alkyl moiety has from about one to about three carbon atoms. The especially preferred lower alkyl moiety has one carbon atom. Specific phosphorous compounds suitable in this regard are bis-dihydroxy-phosphonylmethyl-phosphinic acid and tris-dihydroxyphosphonyl methyl-phoshine oxide.

The synthesis and the properties of bis-hydroxy-phosphonylmethyl-phosphinic acid and tris-dihydroxyphosphonylmethyl-phosphine oxide are disclosed by Maier, Colloq. Int. Cent. Nat. Rech. Sci.(1970) Vol. 182, pp. 47-52 which is incorporated herein by reference. The phosphorous compounds can also be prepared according to the method disclosed by Knollmueller in U.S. Pat. No. 3,534,125 incorporated herein by reference. This synthesis comprises converting bis(hydroxymethyl) phosphinic acid by means of thionylchloride to bis(chloromethyl) phosphinic acid chloride. The bis(chloromethyl) phosphinic acid chloride is reacted with an organic alcohol or hydrocarbyl hydroxyl compound to produce an intermediate chloromethyl ester. The chloromethyl ester is then reacted with a tri-hydrocarbyl phosphite by the Michaelis-Arbusov reaction. The ester obtained from this latter reaction is then heated with a strong acid such as hydrochloric acid to hydrolyze it to the phosphinic acid phosphorous containing compounds employed according to the present invention.

Upon obtaining the phosphinic acid phosphorous compound, it may be neutralized with an appropriate base such as an alkaline earth metal ion or alkali metal ion base. The salt of the phosphinic acid compound may then be employed per se as a diamagnetic compound according to the present invention for affecting NMR spectra or the phosphinic acid salt may be reacted with a metal ion salt (i.e. a paramagnetic or ferromagnetic metal ion salt) in a matathesis reaction whereby the phosphinic acid compound will complex with the metal ion ion.

The complexes are then administered to a host and the host, thus treated is subjected to NMR analysis. This analysis is best understood by a brief explanation of NMR phenomenon.

Nuclear magnetic resonance phenomenon occurs in atomic nuclei having a non-zero nuclear spin. Due to its spin each nucleus exhibits a magnetic moment, so that, when a sample composed of such nuclei is placed in a static, homogeneous magnetic field, $B_o$, a greater number of nuclear magnetic moments align with the field to produce a net macroscopic magnetization M (also referred to as longitudinal magnetization) in the direction of the field. Under the influence of the magnetic field $B_o$, magnetization M precesses about the axis of the field at a frequency which is dependent on the strength of the applied magnetic field and on the characteristics of the nuclei. The angular precession frequency, $\omega$, also referred to as the Larmor frequency, is given by the Larmor equation $\omega = \gamma \cdot B_o$ in which $\gamma$ is the gyromagnetic ratio which is constant for each NMR isotope an wherein $B_o$ is the magnetic field acting upon the nuclear spins. It will be thus apparent that the resonant frequency is dependent on the strength of the magnetic field in which the sample is positioned.

The orientation of magnetization M, normally directed along the magnetic field $B_o$, may be perturbed by the application of a magnetic field oscillating at the Larmor frequency. Typically, such a magnetic field, designated $B_l$, is applied in a plane orthogonal to the direction of the static magnetic field by means of a radio frequency (RF) pulse through coils connected to a radio-frequency-transmitting apparatus. The effect of field $B_l$ is to rotate magnetization M about the direction of the $B_l$ field. This may be best visualized if the motion of magnetization M due to the application of RF pulses is considered in a Cartesian coordinate system which rotates at a frequency substantially equal to the resonant frequency about the main magnetic field $B_o$ in the same direction in which the magnetization M precesses (i.e., the rotating frame). In this case the positive direction of the Z-axis is typically chosen to be directed along $B_o$. In the rotating frame Z is designated Z' to distinguish it from the fixed-coordinate system. Similarly, the X- and Y-axes are designated X' and Y'. Bearing this in mind, the effect of an RF pulse, then, is to rotate magnetization M, for example, from its direction along the positive Z' axis toward the transverse plane defined by the X' and Y' axes. An RF pulse having either sufficient magnitude or duration to rotate magnetization M into the transverse plane (i.e., 90° from the direction of the $B_o$ field) is conveniently referred to as a 90° RF pulse. Similarly, proper selection of either magnitude and/or duration of an RF pulse will cause magnetization M to change direction from the positive Z' axis to the negative Z' axis. This kind of an RF pulse is referred to as a 180° RF pulse, or for obvious reasons, as an inverting pulse. It should be noted that a 90° or a 180° RF pulse will rotate magnetization M through the corresponding number of degrees form any initial direction of magnetization M. It should be further noted that an NMR signal will only be observed if magnetization M has a net transverse component in the transverse plane (perpendicular to $B_o$). Assuming an initial orientation of magnetization M in the direction of the $B_o$ field, a 90° RF pulse produces maximum net transverse magnetization in the transverse plane since all of magnetization M is in that plane, while a 180° RF pulse does not produce any transverse magnetization. The 180° RF pulses are frequently utilized to produced NMR spin-echo signals.

RF pulses may be selective or nonselective. Selective pulses are typically modulated to have a predetermined frequency content so as to excite nuclear spins situated in preselected regions of the sample having precession frequencies as predicted by the Larmor equation. In NMR imaging the selective pulses are applied in the presence of localizing magnetic field gradients (discussed hereinbelow). Nonselective pulses generally affect all of the nuclear spins situated within the field of the RF pulse transmitter coil and are typically applied in the absence of localizing magnetic field gradients.

Upon cessation of the RF excitation, magnetization M due to the excited nuclear spins begin to return to equilibrium under the influence of the $B_o$ field. As it does so, the magnetic flux intercepts the conductors of a RF pickup coil and induces therein a voltage, termed the NMR signal. This return to equilibrium has associated therewith two exponential time constants associated with longitudinal and transverse magnetizations. The time constants characterize the rate of return to equilibrium of these magnetization components following the application of perturbing RF pulses. The first time constant is referred to as the spin-lattice relaxation time ($T_1$) and is the constant for the longitudinal magnetization to return to its equilibrium value. Spin-spin relaxation time ($T_2$) is the constant for the transverse magnetization to return to its equilibrium value in a perfectly homogeneous field $B_o$. In fields having inhomogeneities, the time constant for transverse magnetization is governed by a constant denoted $T_2^*$, with $T_2^*$ being less than $T_2$. The values of spin-lattice and spin-spin relaxation times for protons vary widely with tissue type. For biological tissue $T_1$ and $T_2$ values may range from 30 msec. to 3 sec., and 5 msec. to 3 sec., respectively.

There remains to be considered the use of magnetic field gradients to encode spatial information (used to reconstruct images, for example) into NMR signals. Typically, three such gradients are necessary:

$G_x(t) = \delta B_o / \delta x$, $G_y(t) = \delta B_o / \delta y$, and $G_z(t) = \delta B_o / \delta z$.

The $G_x$, $G_y$, and $G_z$ gradients are constant throughout the imaging slice, but their magnitudes are typically time dependent. The magnetic fields associated with the gradients are denoted, respectively, $b_x$, $b_y$, and $b_z$, wherein $b_x = G_x(t)x$, $b_y = G_y(t)y$, $b_z = G_z(t)z$ within the volume.

In general, $T_1$ relaxation time is measured by means of either a progressive saturation or an inversion recovery technique, while $T_2$ relaxation time is typically measured by multiple spin-echo technique. These techniques, which are well known to those skilled in the art, will be described hereinbelow in the context of a two-dimension Fourier transform (2DFT) NMR Imaging technique (commonly referred to as spin warp).

The progressive saturation technique can be employed using four spin-warp pulse sequence which can be designated 1–4, 5–8, 9–12, and 13–16, along the horizontal axis. A complete pulse sequence (scan) would typically consist of three amplitudes (128, 256, or 512) which are substantially identical to one another, with the exception that a different amplitude of the phase-encoding pulse gradient $G_y$ is employed in each (assuming no averaging).

One example comprising intervals 1–4 will now be described in detail. In interval 1, a selective 90° RF excitation pulse is applied in the presence of a positive $G_z$ gradient pulse so as to preferentially excite nuclear spins in a predetermined region of a sample object having precession frequencies as predicted by the Larmor equation. A negative $G_z$ pulse is applied in interval 2 to rephase nuclear spins excited in inteval 1. Typically, the $G_z$ pulses are selected such that the time integral of the gradient pulse waveform over interval 2 is equal to a negative one half of the time integral of the gradient pulse over inteval 1. $G_x$ and $G_y$ gradient pulses are also applied simultaneously with the $G_z$ gradient pulse in interval 2. The function of the $G_y$ gradient pulse is, as alluded to hereinabove, to encode phase information into the excited nuclear spins. The purpose of the $B_x$ gradient pulse is to dephase the excited nuclear spins by a predetermined amount to delay the occurrence of the NMR spin-echo signal in interval 4. The spin echo is produced by the application of a 180° RF pulse in interval 3. The spin echo is sampled in interval 4 in the presences of a linear $G_x$ readout gradient. The NMR information encoded in the NMR signal by the phase encoding and the readout gradient is recovered in a well-known manner using two-dimensional Fourier transform techniques.

The excitation/sampling process described hereinabove is repeated in each of the pulse sequences until the $G_y$ gradient is sequenced through its range of amplitudes (128, 256, etc.). The repetition time TR, is the period of time between the beginning of one pulse sequence view and the beginning of a succeeding (essentially identical) pulse sequence of the next. TR is measured between the mean application of 90° RF pulses in succeeding steps. Typically, TR is not varied in the course of a single scan. However, TR can be varied from one scan to the next. If TR is selected to be equal to or greater than approximately five times the $T_1$ constant of a sample, then all of the longitudinal magnetization will have returned to equilibrium and the image resulting from such a scan would have little or no dependence on $T_1$. Shortening TR to be less than five times $T_1$ increases the $T_1$ contribution in the image.

The pulse sequence may be modified, for example, to include magnetic field gradient pulses immediately preceding and following the 180° RF pulses (such as the ones in intervals 3, 7, 11 . . ., etc.) to reduce the effects of spurious NMR signals produced when regions in the sample object experience less than 180° RF excitation. These gradient pulses (termed pre-crusher and crusher) would be applied in the direction in which most of the sample is disposed. In the case of a whole-body system utilizing a solenoidal magnet, the $G_z$ gradient would be pulsed. Another way in which the pulse sequence can be modified is to use selective 180° RF pulses so as to lessen the sampling bandwidth requirements thereby to reduce aliasing artifacts. Such selective 180° RF pulses would be applied in the presence of a G magnetic field gradient pulse.

In a typical pulse sequence, the duration to the $G_z$ gradient in interval is approximately 4 msec., while the duration of the 90° RF pulse (typically modulated by a Sin x/x function) is about 3.2 msec. from beginning to end. Similarly, the $G_x$, $G_y$, and $G_z$ gradients in interval 2 are applied for approximately 4 msec. The readout $G_x$ gradient in interval 4 is selected to be approximately 8 msec. long. Magnetic field gradient pulses preceding and following the 180° RF pulses, if used, are each 2–4 msec. The 180° RF pulse is selected to have approximately twice the amplitude of the 90° RF pulse and is also 3.2 msec. long. It will be appreciated, therefore, that a typical TR time cannot be shorter than the sum of the various times indicated, pulse various power supply and amplifier recovery times. This implies that TR is typically about 30–33 msec.

The inversion recovery technique for introduction a $T_1$ dependence in an NMR image employs a 180° RF pulse prior to the 90° RF excitation pulse. Thus, a 180° RF pulse applied in interval 1 is followed in interval 2 by the 90° RF pulse. The time between the mean application of the 180° and the 90° pulses is referred to as inversion time (denoted TI). Variable inversion times can be selected, although a constant value is used in any given scan. As is known, the effect of the 180° RF pulse is to invert the longitudinal magnetization. The extent to which the longitudinal magnetization recovers is detected by the 90° pulse. As may be anticipated, the degree of recovery is dependent on the inversion time and the $T_1$ constant of the sample object. It will be apparent, therefore, that varying TI will introduce a different degree of $T_1$ dependence into the NMR signal and, hence, the image. As before, a magnetic field gradient pulse can be applied (e.g., a 4 msec. long $G_z$ gradient pulse) during TI to reduce the effects of any spurious NMR signals following the 180° RF pulse.

In an inversion recovery pulse sequence, the time (denoted TE) of occurrence of the spin-echo signal is reduced to a minimum and a TR of the order of 1–2 seconds is selected. The duration of the 180° RF pulse (which need not be modulated by a Sin x/x function) in interval 1 may be between 0.250 and 0.700 msec.

A multiple spin-echo sequence may be used to acquire $T_2$ image information. This pulse sequence is substantially identical to the previously described pulse sequence with the exception that multiple spin-echo signals are produced in intervals 6 and 8 by the application of 180° RF pulses in intervals 5 and 7. The spin-echo signals occur at echo times designated TE1, TE2 and TE3. As before, succeeding spin-echo signals are sampled in the presence of contemporaneously applied linear readout $G_x$ gradient pulses. As suggested by the "$T_2$ Decay" the spin echo amplitudes decay with a $T_2$ time constant. Of course, it will be recognized that fewer or more spin-echo signals can be produced by decreasing and increasing the number of 180° RF pulses. The maximum useful number of spin-echo signals is limited by the $T_2$ relaxation time of the sample object.

The pulse sequences described hereinbefore are utilized for imaging sample objects such as biological tissue having what will be referred to as "normal" $T_1$ and $T_2$ relaxation constants. These pulse sequences, particularly the timing parameters, must be modified when imaging sample objects which are under the influence of particle systems which tend to shorten normal $T_1$ and $T_2$ values. Thus, when considering, e.g., spin-echo imaging the pulse sequence, the echo time TE should be less than $T_2$ to achieve reasonable signal intensity. To image short relaxation time complexes, it is necessary to correspondingly shorten TE as $T_1$, $T_2$ are decreased. The minimum echo time is established by the cumulative time requirements of the pulse sequence as determined by the gradient pulses, 180° RF pulse, precrusher and crusher pulses and the readout signal gradient requirement. These minimum echo times total, in a conventional pulse sequence, to about 16 msec. for a 0.5 T and 33 msec. for a 1.5 T magnet system.

Several approaches may be taken to compress the echo time for short relaxation characteristic particle system imaging. Consider operating at the same $B_o$ main magnet field strength as used for conventional body imaging, e.g., 1.5 T. Consider further that the TE of the complex may be in the range of ⅓ to 1/10 that for biological tissue or e.g., 3.3–11 msec. and that the pulse sequence is uniformly compressed. The gradient and RF pulses must then deliver the same energy in ⅓ to 1/10 the time and, therefore, require peak pulse amplitudes between 3 and 10x the requirement for a conventional TE of about 33 msec.

Alternatively, the main field $B_o$ can be reduced a factor of 3–10x to a value of 0.15–0.5 T for the short echo time image allowing the RF and gradient pulse power amplitudes in the time compressed pulse sequence to remain at the same peak value as employed for biological tissue imaging at e.g., TE=33 msec. This approach is less costly as it is less demanding of pulse power amplifiers. The trade-off, however, is the delay introduced in switching the $B_o$ field.

To image the long relaxation characteristic materials, consider TE values of 3–10x the conventional TE minimum of 33 msec. Operating at a field strength of 1.5 T requires a reduction in RF and gradient pulse amplitudes by a factor of 3–10x and a uniformly stretched pulse sequence.

In utilizing the complexes of the present invention the presence and locations of lesions may be identified by injecting the complex into a mammalian host, waiting a suitable period for the complex to concentrate in the lesion, and then imaging the host twice. Once using a conventional pulse sequence to establish a reference image, and then a second time using a tailored pulse sequence (short or long) to match the short or long relaxation time characteristic of the particular complex system employed.

A water-soluble anionic coordination-complex of the trivalent, paramagnetic-ion gadolinium and bis-dihydroxyphosphonyl methyl-phosphinic acid (BDP) is prepared using the above described method and has the formula:

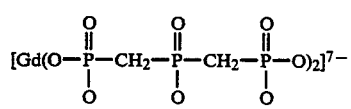

The above compound (Gd BDP) is employed as a contrast agent for NMR imaging. The metal-chelating ligand bis-dihydroxyphosphonylmethyl-phosphinic acid was found not to be readily hydrolyzable by the usual, phosphate hydrolyzing enzymes abundant in living tissues. Additionally, at a magnetic field of 0.47 Tesla (T), the contrasting capability measured by $1/T_1$ of the bis-dihydroxyphosphonylmethyl-phosphinic acid-chelated gadolinium in NMR analysis using the inversion recovery method is higher than that of uncomplexed gadolinium ($Gd^{3+}$). These results are unexpected in that ordinarily when a paramagnetic metal ion is chelated by an organic ligand, it is expected that the relaxation enhancement effect on the surrounding water molecules in the tissue of a mammalian host would be significantly reduced. Since this effect is the source for the contrast enhancement in NMR imaging, such a reduction results in a decreased contrast capability of the complexed metal ion relative to the uncomplexed one. As noted previously, complexing of the paramagnetic metal ions is effected in order to reduce the toxicity of such metal ions in mammalian hosts. The trade-off in forming the complex is to obtain contrast agents that are less toxic but still have a measurable effect on NMR imaging. It was unexpected to find that the gadolinium complex of this dihydroxyphosphonylmethylphosphinic acid has an effect which is not less but rather more pronounced (i.e. shorter relaxation times) than uncomplexed gadolinium in NMR imaging.

At 9.4 T, Gd BDP relaxation times are found to be higher than $Gd^{3+}$. Similar results were noted for Gd EDTA (ethylene diamine tetracetic acid) complexes at both 0.47 T and 9.4 T.

In addition to its application as a contrast agent for NMR imaging, the complexes described and disclosed herein can be used in any scientific or technological context in which magnetic differentiation between compartments is needed. As an illustration, but not by way of limitation, these complexes are useful in NMR spectroscopic studies of membrane transport of various metabolites.

Although the invention has been described by reference to some embodiments, it is not intended that the novel complexes and the method for NMR analysis employing the complexes are to be limited thereby but that modifications thereof are intended to be included as falling within the broad spirit and scope of the foregoing disclosure and the following claims.

What is claimed is:

1. A method for NMR analysis comprising administering to a host an NMR signal affecting amount of a complex of
    (a) a metal ion selected from a member of the group consisting of metal ions having atomic number 21 to 29 inclusive, 42 to 44 inclusive and the lanthanides having atomic numbers 57 to 70 inclusive, and
    (b) an organophosphorous metal ion chelating ligand comprising a phosphonylorgano phosphinate to form complexes of the formula:

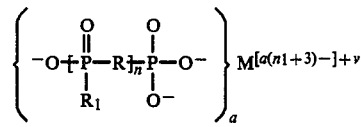

wherein
n=2 to about 100;
$n_1$=the number of negative charges in n

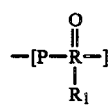

groups;

a=1, 2, or 3;
M=a metal ion described hereinabove;
v=the valence of M;
$R_1 = O^-$ or an organophosphenate comprising

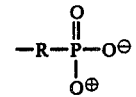

R=alkyl moiety, whether branched chain or straight chain, cyclic hydrocarbon moiety having from 3 to about 10 carbon atoms, said cyclic hydrocarbon moiety being saturated or unsaturated and including fused ring cyclic hydrocarbon moieties; heterocyclic hydrocarbon moieties having from 1 to 2 hetercyclic nitrogen, phosphorous, sulfur or oxygen atoms in said heterocyclic ring, said heterocyclic hydrocarbon moiety being saturated or unsaturated, and subjecting said host to NMR analysis.

2. The method of claim 1 where said phosphinate ligand is a bis-dihydroxyphosphonyl-loweralkyl-phosphinic acid.

3. The method of claim 1 where said phosphinate ligand is a tris-dihydroxyphosphonyl-loweralkyl-phosphine oxide.

4. The method of claim 2 where said lower alkyl moiety includes straight chain or branched chain alkyl radicals having from 1 to about 3 carbon atoms.

5. The method of claim 3 where said lower alkyl moiety includes straight chain or branched chain alkyl radicals having from 1 to about 3 carbon atoms.

6. The method of claim 2 where said phosphorous compound is bis-dihydroxyphosphonylmethyl-phosphinic acid.

7. The method of claim 3 where said phosphorous compound is tris-dihydroxyphosphonylmethyl-phosphine oxide.

8. The method of claim 1 where said complex is a water soluble anionic coordination-complex of a metal ion selected from a member of the group consisting of the lanthanide metal ions having atomic numbers 57 to 70 inclusive.

9. The method of claim 1 where said

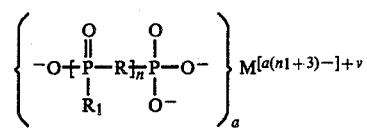

where R is a lower alkyl moiety l, n, $n_1$ and v are defined previously and M is selected from a member of the group consisting of lanthanide metal ions, ions of the metals having atomic numbers 21 to 29 inclusive, 42 to 44 inclusive.

10. The method of claim 9 where R is a methyl moiety.

11. The method of claim 1 where said complex has the formula:

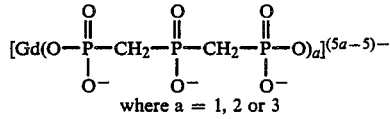

where a = 1, 2 or 3 where a 1, 2, or 3

12. The method of claim 1 where said host is a mammalian host.